United States Patent
Harimoto et al.

(10) Patent No.: US 12,049,640 B2
(45) Date of Patent: Jul. 30, 2024

(54) CELL ADHESIVE MATERIAL

(71) Applicant: TORAY INDUSTRIES, INC., Tokyo (JP)

(72) Inventors: Kenichi Harimoto, Otsu (JP); Hirokazu Sakaguchi, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 1015 days.

(21) Appl. No.: 16/971,358

(22) PCT Filed: Mar. 11, 2019

(86) PCT No.: PCT/JP2019/009713
§ 371 (c)(1),
(2) Date: Aug. 20, 2020

(87) PCT Pub. No.: WO2019/176860
PCT Pub. Date: Sep. 19, 2019

(65) Prior Publication Data
US 2021/0054333 A1   Feb. 25, 2021

(30) Foreign Application Priority Data

Mar. 15, 2018 (JP) .................. 2018-047504

(51) Int. Cl.
| | |
|---|---|
| C12N 5/00 | (2006.01) |
| A61L 31/04 | (2006.01) |
| A61L 31/06 | (2006.01) |
| A61L 31/10 | (2006.01) |
| A61L 31/12 | (2006.01) |
| C07K 17/06 | (2006.01) |

(52) U.S. Cl.
CPC .......... C12N 5/0068 (2013.01); A61L 31/048 (2013.01); A61L 31/06 (2013.01); A61L 31/10 (2013.01); A61L 31/125 (2013.01); C07K 17/06 (2013.01); C12N 2533/00 (2013.01)

(58) Field of Classification Search
None
See application file for complete search history.

(56) References Cited

U.S. PATENT DOCUMENTS

| | | | |
|---|---|---|---|
| 6,191,113 B1 | 2/2001 | Nakahara et al. | |
| 2003/0113478 A1* | 6/2003 | Dang | ............... A61L 29/085 |
| | | | 427/535 |
| 2009/0030505 A1* | 1/2009 | Kleiner | ............... A61P 9/14 |
| | | | 623/1.42 |

FOREIGN PATENT DOCUMENTS

| | | |
|---|---|---|
| JP | 2006-272002 A | 10/2006 |
| JP | 2007-159874 A | 6/2007 |
| JP | 2010-184022 A | 8/2010 |
| WO | WO 90/11297 A1 | 10/1990 |
| WO | WO 97/15598 A1 | 5/1997 |
| WO | WO 2010/033925 A2 | 3/2010 |

OTHER PUBLICATIONS

International Search Report, issued in PCT/JP2019/009713, dated Jun. 4, 2019.
Written Opinion of the International Searching Authority, issued in PCT/JP2019/009713, dated Jun. 4, 2019.

* cited by examiner

*Primary Examiner* — David J Blanchard
*Assistant Examiner* — Sarah J Chickos
(74) *Attorney, Agent, or Firm* — Birch, Stewart, Kolasch & Birch, LLP

(57) ABSTRACT

A cell adhesive substrate comprising a substratum, on a surface of which a peptide group is immobilized, wherein the peptide group comprises a peptide containing 40% or more and 75% or less of one or two or more of basic amino acid residues selected from the group consisting of lysine, arginine and histidine and 25% or more of one or two or more of hydrophobic amino acid residues selected from the group consisting of leucine, isoleucine, glycine, alanine, valine, phenylalanine, proline, tryptophan and methionine. There is provided a cell adhesive substrate that is unlikely to cause an immune reaction and can maintain a cell adhesion effect for a long time.

9 Claims, No Drawings

CELL ADHESIVE MATERIAL

TECHNICAL FIELD

The present invention relates to a cell adhesive substrate suitable as a cell culture plate or a scaffold material for cell.

BACKGROUND ART

There are various types of medical substratums used for implantable devices and the like, such as polymers, metals and ceramics, and those having physical properties suitable for each use of the device are selected. A common requirement for these substratums is biocompatibility. A substratum having high biocompatibility does not cause an immune reaction in the body after transplantation, and the substratum surface is quickly covered with cells. Therefore, a technique for improving cell adhesion on the substratum surface has been developed for a long time. In particular, a substratum with improved cell adhesion by immobilizing a specific molecule on the substratum surface has been developed. As a molecule which improves cell adhesion, extracellular matrix (ECM) molecules such as collagen, fibronectin and laminin that are cell adhesion proteins are known. Also, peptides obtained by extracting a partial amino acid sequence of these ECM molecules are known. It is also known that polylysine obtained by polymerizing the amino acid lysine exhibits high cell adhesion in vitro. Furthermore, a substratum on which a peptide having a sequence that enhances affinity with specific cells is immobilized is known. For example, in Patent Document 1, a synthetic peptide having an amino acid sequence that exhibits strong affinity for cell surface proteins and sugar chains is immobilized on the substratum surface by a chemical bond. Patent Document 2 has developed a gel in which a peptide having an amino acid sequence having a function of promoting cell migration and proliferation is chemically bound. Various developments have also been made on the method of fixing to the substratum surface. For example, in Patent Document 3, a spacer molecule is added to a peptide having a specific sequence having an antibacterial function, and then immobilized on a substratum via the spacer.

PRIOR ART DOCUMENTS

Patent Documents

Patent Document 1: Japanese Patent Laid-open Publication 2007-159874
Patent Document 2: Japanese Patent Laid-open Publication 2006-272002
Patent Document 3: Japanese Patent Laid-open Publication 2010-184022

SUMMARY OF THE INVENTION

Problems to be Solved by the Invention

Since the ECM molecule is of biological origin, it may become an antigenic peptide that causes an immune reaction when it is degraded in vivo. Further, in order to produce a peptide having a specific sequence as in Patent Documents 1 to 3, a special device and high cost are required. On the other hand, polylysine, which is a simple sequence, is excellent in terms of safety and cost, but is unstable in vivo and is released from the surface of the substratum. An immobilization method via a chemical bond is used as a method for stably immobilizing a peptide, but there are problems that physical properties of the substratum are changed and the substratum is degraded depending on the reaction conditions.

An object of the present invention is to provide a cell adhesive substrate that is unlikely to cause an immune reaction and can maintain a cell adhesion effect for a long time.

Solutions to the Problems

In order to solve the above problems, the present invention is a cell adhesive substrate comprising a substratum, on a surface of which a peptide group is immobilized, wherein the peptide group contains a peptide containing 40% or more and 75% or less of one or two or more of basic amino acid residues selected from the group consisting of lysine, arginine and histidine and 25% or more of one or two or more of hydrophobic amino acid residues selected from the group consisting of leucine, isoleucine, glycine, alanine, valine, phenylalanine, proline, tryptophan and methionine.

Effects of the Invention

According to the present invention, a cell adhesive substrate that is unlikely to cause an immune reaction and can maintain a cell adhesion effect for a long time can be obtained.

EMBODIMENTS OF THE INVENTION

Hereinafter, the cell adhesive substrate of the present invention (hereinafter, sometimes simply referred to as "substrate") will be described. In the present specification, "peptide" is used as a term indicating a single molecule peptide, and "peptide group" is used as a term indicating an aggregate of a plurality of peptides.

Cell Adhesive Substrate

Substratum

In the present invention, the cell adhesive substrate is one in which the specific peptide group is immobilized on the surface of the substratum, and is intended to be used for proliferation and expression of cell-specific functions by adhering the cells to the surface of the substratum or inside the substrate.

The raw material of the substratum is not particularly limited, but is preferably a polymer capable of stably adsorbing peptide by hydrophobic interaction as described later. Specific examples of such a polymer include polylactic acid, polyglycolic acid, polycaprolactone, polylactide glycoside, polyether ether ketone, polysulfone, polyvinylidene fluoride, polyphenylene sulfide, polypropylene, polyethylene, polyvinyl chloride, polystyrene, polyethylene terephthalate, polybutylene terephthalate, and copolymers thereof. The material of the substratum is more preferably a material selected from polylactic acid, polyglycolic acid, polycaprolactone, polylactide glycosides, polyether ether ketone, polyvinyl chloride, polystyrene, polyethylene terephthalate, polybutylene terephthalate and copolymers thereof.

Further, in the case of being used as a material for a medical device that is placed in a living body for an arbitrary period for use as a scaffold for cell proliferation, it is particularly preferable to use a so-called bioabsorbable polymer as a raw material of the substratum. The bioabsorbable polymer is a polymer that is degraded in the living body, in which the degradation product is consumed or excreted. In particular, a polymer of one kind of monomer or a copolymer of two or more kinds of monomers selected from the group consisting of lactic acid, caprolactone and glycolic acid, which has low toxicity of degradation product and has a high clinical record, has an excellent track record of use as a bioabsorbable polymer, and thus is preferably used.

The shape of the substratum is not limited, and a shape suitable for the application of the cell adhesive substrate of the present invention can be selected. For example, as the shape of the scaffold material for cell used for culturing cells ex vivo, a fibrous structure such as a knitted fabric, a woven fabric or a non-woven fabric; or a shape such as a hollow fiber, film, tube, sponge, bead, porous, gel, dish or plate can be selected. Also, as the shape of the substratum used in a purification device for removing or collecting cells, a fibrous structure such as a knitted fabric, a woven fabric or a non-woven fabric; or a shape such as film, a hollow fiber, sponge, bead or porous can be selected. In addition, as the shape of the substratum of a device to be transplanted and treated in the body, a fiber structure such as a knitted fabric, a woven fabric or a non-woven fabric; or a shape such as a hollow fiber, film, tube, sponge, bead, porous or gel can be selected.

Peptide

"Peptide" generally refers to a compound in which amino acids up to about 50 residues are peptide-bonded, but in the present specification, a so-called polypeptide in which more than 50 amino acid residues are bound is also called a "peptide", regardless of the number of amino acid residues. Further, the content of amino acid residues in a peptide in the present specification is a percentage of the number of target amino acid residues with respect to the total number of amino acid residues constituting the peptide.

In the cell adhesive substrate of the present invention, a peptide group is immobilized on the surface of the substratum as described above, and as a peptide constituting the peptide group, a peptide containing 40% or more and 75% or less of one or two or more of basic amino acid residues selected from the group consisting of lysine, arginine and histidine and 25% or more of one or two or more of hydrophobic amino acid residues selected from the group consisting of leucine, isoleucine, glycine, alanine, valine, phenylalanine, proline, tryptophan and methionine is selected.

As the basic amino acid, arginine or lysine with a high isoelectric point is preferable because it strongly binds to cells by electrostatic interaction. That is, the peptide preferably contains 40% or more and 75% or less of one or two basic amino acid residues selected from the group consisting of lysine and arginine.

As the hydrophobic amino acid, any one or more of leucine, isoleucine, valine and phenylalanine is preferred because it easily forms hydrophobic interaction with the surface of the substratum. That is, the peptide preferably contains 25% or more of one or two or more hydrophobic amino acid residues selected from the group consisting of leucine, isoleucine, valine and phenylalanine.

The peptide preferably contains 40% or more of the above hydrophobic amino acid residues in order to enhance the absorbability to the substratum by the hydrophobic interaction. On the other hand, in order to sufficiently maintain the cell adhesion due to the basic amino acid residues and sufficiently secure solubility in water, the peptide preferably contains 50% or less of the hydrophobic amino acid residues.

The peptide may further contain other amino acid residues as long as it contains the basic amino acid residues and the hydrophobic amino acid residues in the above ranges. However, in order to prevent an electrostatic action of basic amino acid residues from being neutralized, a peptide consisting of basic amino acid residues and hydrophobic amino acid residues is preferred.

Preferred examples of the combination of the basic amino acid and the hydrophobic amino acid include combinations of lysine and phenylalanine, lysine and leucine, lysine and valine, arginine and phenylalanine, arginine and leucine, and arginine and valine. That is, as the peptide, a peptide containing 40% or more and 75% or less of lysine or arginine residues and 25% or more of any of phenylalanine, leucine and valine residues is preferred.

It is particularly preferable that the peptide group immobilized on the substratum is composed of peptides without an ordered amino acid sequence in the constituent amino acid residues including the above-mentioned basic amino acid residues and hydrophobic amino acid residues. Here, the ordered amino acid sequence refers to a sequence based on all or part of the amino acid sequence encoded by the gene of the organism, or an amino acid sequence artificially designed to imitate the sequence. That is, a peptide group composed of peptides without an ordered amino acid sequence is a peptide group composed of peptides without such specific amino acid sequence. As the peptide without an ordered amino acid sequence, specifically, a random copolymer or alternating copolymer of the basic amino acid and the hydrophobic amino acid is preferred. A peptide group without such a specific sequence is unlikely to cause an immune reaction and can be easily synthesized by liquid phase synthesis described later, and thus a cell adhesive substrate can be produced at low cost. Of these, a random copolymer is particularly preferred.

The weight average molecular weight of the peptide group is preferably 1,000 or more, and in order to enhance the cell adhesion function, more preferably 1,500 or more, and further preferably 5,000 or more. On the other hand, when the molecular weight becomes too large, a three-dimensional structure of the peptide may change and the function may be difficult to be expressed, so the weight average molecular weight of the peptide is preferably 30,000 or less, more preferably 15,000 or less, and further preferably 10,000 or less. The weight average molecular weight of the peptide can be measured by gel permeation chromatography (GPC) method as in Measurement Example 1 described later, and can be determined as a conversion value using polystyrene as a standard substance.

When measuring the ratio and molecular weight of amino acid residues of a peptide adsorbed on the surface of the substratum, they can be measured by recovering the peptide from the surface of the substratum with a surfactant solution of sodium dodecyl sulfate or the like, and then analyzing the amino acid sequence by Edman degradation method or MALDI-TOF mass spectrometer.

In the present invention, as the state where the peptide group is immobilized on the surface of the substratum, it is preferable that the peptide is adsorbed on the surface of the substratum without a chemical bond, and further preferable that the peptide is adsorbed only by the hydrophobic interaction. When there is no chemical bond between the peptide and the substratum, only the known degradation products of the peptide and the substratum will be produced, and thus a safety test for unknown components is unnecessary.

The peptide used in the present invention may be used in any of liquid phase synthesis, solid phase synthesis, or genetic engineering synthesis, but it is preferable to use a liquid phase synthesis that can be synthesized by simple equipment since it has an advantage that it can be carried out at a low cost in industrialization. When liquid phase synthesis is used, the peptide can be synthesized by the method shown in the examples.

In order to adsorb the peptide group on the surface of the substratum, the peptide group may be brought into contact with the surface of the substratum and then dried as necessary. The method of bringing the peptide group into contact with the surface of the substratum is not particularly limited, but a method of immersing the substratum in an aqueous solution of the peptide group is preferred. Specific examples include a method of immersing the substratum in an aqueous solution of the peptide group prepared to a concentration of 50 µg/mL to 1000 µg/mL, and allowing to stand under an environment of a temperature of 4° C. to room temperature for about 1 to 12 hours, then removing the supernatant and air drying the substratum for 10 minutes or more.

The immobilization density of the peptide on the surface of the substratum is preferably 0.040 µg/cm$^2$ or more, and more preferably 0.080 µg/cm$^2$ or more and further preferably 0.100 µg/cm$^2$ or more so that the peptide is uniformly immobilized on the surface of the substratum. The immobilization density of the peptide can be confirmed using, for example, a quantitation method of dye adsorbed amount. The quantitation method of dye adsorbed amount is a method of measuring the adsorbed amount on the substratum of Orange2 which is an anionic dye, and specifically, it can be performed by the method of Measurement Example 3 described later. Since 1 mole of Orange2 binds to 1 mole of cationic residues (arginine and lysine), the amount of cationic residues per unit area of the surface of the substratum can be calculated from the amount of adsorbed Orange2. Based on the amount of cationic residues per unit area of the surface of the substratum, the ratio of cationic residues in the peptide and the molecular weight of each residue, the peptide immobilization density (µg/cm$^2$) which is an amount of peptide adsorbed per unit area of the surface of the substratum can be calculated.

EXAMPLES

[Measurement Example 1] Weight Average Molecular Weight of Peptide Group

A group of peptides with protecting groups was dissolved in a mobile phase and passed through a 0.45 µm syringe filter (DISMIC-13HP; ADVANTEC) to remove impurities and the like, then measured by the GPC method to calculate the weight average molecular weight of the peptides. The conditions for GPC measurement are as follows.
Device name: Prominence (Shimadzu Corporation)
Mobile phase: 10 mM lithium bromide (Wako Pure Chemical Industries) in dimethylformamide (HPLC) (Wako Pure Chemical Industries) solution
Flow rate: 0.5 mL/min
Column: Tskgel Super AW3000 (φ6.0 mm×150 mm; Tosoh)
Detector: UV (254 nm), RI
Column, detector temperature: 40° C.
Standard material: Polystyrene

[Measurement Example 2] Content of Amino Acid Residues in Peptide Group

It measured using an NMR measuring device (JNM-EX270, JEOL). The synthesized peptide group was dissolved in heavy water and measured by $^1$H-NMR. Spectra of 6.5 to 7.5 ppm represent protons of a phenyl group of phenylalanine, and spectra of 1 to 2 ppm represent protons bonded to a carbon of the side chain of lysine. Setting the value obtained by dividing an integral value of the phenylalanine spectrum intensity by the number of phenylalanine protons as F, and the value obtained by dividing the integral value of the lysine spectrum intensity by the number of lysine protons as K, the content of phenylalanine residues and the content of lysine residues can be each calculated as follows.

Percentage of phenylalanine residue content=$F/(F+K)\times100$

Percentage of lysine residue content=$K/(F+K)\times100$.

[Measurement Example 3] Peptide Immobilization Density 10 mg of Orange2 (Wako Pure Chemical Industries) was weighed and dissolved in 50 mL of pH 4.0 acetate buffer to prepare a staining solution. When measuring the peptide immobilization density of a 12-well plate (Falcon) surface-immobilized with a peptide group, first, 1 mL each of a staining solution was added to each well and allowed to stand at 37° C. for 1 hour, then the staining solution was aspirated to be removed, 1.5 mL of a 1 mM aqueous sodium hydroxide solution was added to each well, and the mixture was shaken for 30 minutes to prepare an Orange2 extract. When measuring the peptide immobilization density of a film surface-immobilized with a peptide group, one film with the surface-immobilized with a peptide group was placed in each well of a 12-well plate, 1 mL of a staining solution was added to each well, and the mixture was shaken at 37° C. for 1 hour, then the staining solution was aspirated to be removed. Thereafter, the film was transferred to a new 12-well plate, 1.5 mL of a 1 mM aqueous sodium hydroxide solution was added to each well, and the mixture was shaken for 30 minutes to prepare an Orange2 extract.

The staining solution was diluted with a 1 mM aqueous sodium hydroxide solution to 2.0, 1.5, 1.0, 0.5, 0.2, 0.15, 0.10, and 0.05 µg/mL, respectively, and used as samples for a calibration curve.

300 µL each of the Orange2 extract and the calibration curve sample obtained as described above were placed in a 96-well plate (IWAKI), and the absorbance at wavelengths 482 nm and 650 nm was measured using a microplate reader (Molecular Device SpectraMax M5). The absorbance at 482 nm was corrected using the absorbance at 650 nm as a baseline. A calibration curve was prepared by linear approximation from the corrected value of the absorbance at 482 nm and the concentration of the calibration curve sample. The corrected value of the absorbance of the Orange2 extract sample was applied to the calibration curve to calculate the concentration of Orang2 in the Orang2 extract. When the concentration of Orange2 is C (µg/mL) and the surface area of the substratum in contact with the staining solution is S (cm$^2$), the adsorption amount density X (µg/cm$^2$) of Orange2 is calculated by the following formula.

$X=C\times1.5/S$

When the molecular weight of Orenge2 is 350.32, the molecular weight of the lysine residue in the peptide is 128.17, and the molecular weight of the phenylalanine residue in the peptide is 147.18, the peptide immobilization density Y ($\mu g/cm^2$) can be calculated by the following formula.

$$Y=(X/350.32)\times128.17+(X/350.32)\times(F/K)\times147.18$$

[Measurement Example 4] Cell Adhesion Ratio

The cell adhesion performance was evaluated by calculating the cell adhesion ratio according to the following procedure. 1 mL of the cell suspension of IMS-32 (Cosmo Bio) prepared at a concentration of 50,000 cells/mL was added to each well of a 24-well plate, and cultured in an incubator (Thermo Fisher) under an environment of a temperature of 37° C. and 5% $CO_2$. On the next day, the supernatant was removed, 500 µL each of a 4% paraformaldehyde-containing PBS (phosphate buffered saline) solution (Wako Pure Chemical) was added to each well, and the cells were allowed to stand for 5 minutes to fix the cells. The supernatant was removed, and 500 µL each of PBS (Wako Pure Chemical) was added to each well for washing, which was repeated three times. After washing, 200 µL of a DAPI (Wako Pure Chemical No.) aqueous solution prepared to 1 µg/mL was added to each well to stain the nucleus. Using a fluorescence microscope (Olympus), each well was randomly photographed at 5 points. The number of cells in the photograph was counted using image analysis software (ImageJ), and the cell density (cells/$mm^2$) was measured. The measured cell density is divided by the theoretical cell density based on the number of seeded cells, and is expressed as a percentage to obtain the cell adhesion ratio.

Peptide-Immobilized Cell Culture Plate

Example 1

Synthesis of Peptide 300 mg of N-Cbz-Lys-NPC (WATANABE CHEMICAL) and 214 mg of Phe-NPC (WATANABE CHEMICAL) were collected in a 100 mL two-necked recovery flask and placed in an argon atmosphere. This was dissolved in 1.5 mL of dimethylacetamide (Wako Pure Chemical Industries), 38 µL of normal butylamine prepared to a concentration of 1 M with dimethylacetamide was added thereto, and the mixture was reacted at 100° C. for 8 hours. The reacted mixture was added to 40 mL of diethyl ether to precipitate a group of peptides with protecting groups. For purification, the precipitate was recovered, dissolved in 4 mL of chloroform, added to 40 mL of diethyl ether, and reprecipitated. This operation was performed twice to obtain the group of peptides with protecting groups. Using a sample prepared by dissolving 200 mg of the obtained group of peptides with protecting groups in 5.7 mL of trifluoroacetic acid, the weight average molecular weight and the content of amino acid residues were measured according to Measurement Examples 1 and 2.

For deprotection, the group of peptides with protecting groups was each collected in a 100 mL recovery flask and dissolved in trifluoroacetic acid (Wako Pure Chemical Industries), then hydrogen bromide (30% acetic acid solution, Wako Pure Chemical Industries) in an amount 1/10 that of trifluoroacetic acid was added thereto, and the mixture was reacted at room temperature for 2 hours. The reacted mixture was added to 100 mL of diethyl ether to precipitate the peptide group. For purification, the precipitate was dissolved in 4 mL of a 50% aqueous methanol solution, added to 60 mL of diethyl ether, and reprecipitated. This operation was performed twice. The purified precipitate was dissolved in water and freeze-dried to obtain a peptide group.

Immobilization on Substratum 10 mg of the purified peptide group was weighed and dissolved in 10 mL of PBS(-) (Wako Pure Chemical Industries) to prepare a peptide stock solution with a concentration of 1 mg/mL. This peptide stock solution was further diluted 20 times to prepare a peptide solution for immobilization.

This peptide solution for immobilization was added to a polystyrene 12-well plate (Falcon) in an amount of 1 mL per well, and allowed to stand at room temperature overnight, and then the peptide solution was removed. Thereafter, an operation of adding 1 mL of ion-exchanged water to each well and removing it was repeated three times for washing, and the wells were air-dried to obtain a cell culture plate in which a peptide group in which lysine/phenylalanine were randomly arranged was immobilized on the bottom surface of the well.

Example 2

A cell culture plate was obtained in the same manner as in Example 1 except for changing the addition amount of normal butylamine to 19 µL. The weight average molecular weight and the content of amino acid residues were measured using a sample prepared by dissolving 260 mg of the obtained group of peptides with protecting groups in 7.4 mL of trifluoroacetic acid.

Example 3

A cell culture plate was obtained in the same manner as in Example 1 except for changing the addition amount of normal butylamine to 75 µL. The weight average molecular weight and the content of amino acid residues were measured using a sample prepared by dissolving 270 mg of the obtained group of peptides with protecting groups in 7.7 mL of trifluoroacetic acid.

Example 4

A cell culture plate was obtained in the same manner as in Example 1 except for changing the addition amount of normal butylamine to 150 µL. The weight average molecular weight and the content of amino acid residues were measured using a sample prepared by dissolving 170 mg of the obtained group of peptides with protecting groups in 4.8 mL of trifluoroacetic acid.

Example 5

A cell culture plate was obtained in the same manner as in Example 1 except for changing the amount to 150 mg of N-Cbz-Lys-NPC and 321 mg of Phe-NPC. The weight average molecular weight and the content of amino acid residues were measured using a sample prepared by dissolving 138 mg of the obtained group of peptides with protecting groups in 3.9 mL of trifluoroacetic acid.

Example 6

A cell culture plate was obtained in the same manner as in Example 1 except for changing the amount to 450 mg of N-Cbz-Lys-NPC and 107 mg of Phe-NPC. The weight average molecular weight and the content of amino acid residues were measured using a sample prepared by dissolving 282 mg of the obtained group of peptides with protecting groups in 8.0 mL of trifluoroacetic acid.

Example 7

A cell culture plate was obtained in the same manner as in Example 1 except that, as a peptide group, a peptide solution for immobilization was prepared using a peptide (weight average molecular weight 1,417) consisting of 10 amino acid residues, a sequence in which lysine residues and phenylalanine residues are alternately repeated, which was synthesized by entrusting to Sigma-Aldrich Co., Ltd.

Comparative Example 1

A cell culture plate was obtained in the same manner as in Example 1 except that a peptide solution for immobilization was prepared using commercially available polylysine (Sigma-Aldrich) as a peptide group.

Peptide-Immobilized PCL/PLA Film

Example 8

Preparation of Film Composed of L-Lactic Acid/ε-Caprolactone Copolymer (LA/CL Copolymer)

50.0 g of L-lactide (PURASORB L; PURAC) and 38.5 mL of ε-caprolactone (Wako Pure Chemical Industries) were collected as monomers in a separable flask. The flask was placed in an argon atmosphere, 0.81 g of tin(II) octylate (Wako Pure Chemical Industries) dissolved in 14.5 mL of toluene (super dehydrated) (Wako Pure Chemical Industries) as a catalyst and ion-exchanged water as a co-initiator were added so as to have a monomers/co-initiator ratio of 142.9, and a cocatalyst reaction was performed at 90° C. for 1 hour, followed by a copolymerization reaction at 150° C. for 6 hours to obtain a crude copolymer.

The obtained crude copolymer was dissolved in 100 mL of chloroform, and the solution was added dropwise to 1400 mL of stirred methanol to obtain a precipitate. This operation was repeated three times for purification, and the precipitate was dried under reduced pressure at 70° C. to obtain a macromer.

65 g of the macromer, 2.4 g of 4,4-dimethylaminopyridinium p-toluenesulfonate (synthetic product) as a catalyst and 0.86 g of 4,4-dimethylaminopyridine (Wako Pure Chemical Industries) were collected. These were placed in an argon atmosphere and dissolved in dichloromethane (dehydrated) (Wako Pure Chemical Industries) so as to have a concentrations of 30% by weight, and 12 g of dicyclohexylcarbodiimide (Sigma-Aldrich) that is a condensing agent dissolved in 40 mL of dichloromethane was added, then the mixture was subjected to condensation polymerization at room temperature for 2 days.

To the reaction mixture was added 250 mL of chloroform, and the resulting mixture was added dropwise to 4,000 mL of stirred methanol to obtain a precipitate. This precipitate was dissolved in 400 mL of chloroform, and the solution was added dropwise to 4,000 mL of stirred methanol to obtain a precipitate. This operation was repeated twice for purification to obtain a LA/CL copolymer as a precipitate.

The LA/CL copolymer was dried under reduced pressure, dissolved in chloroform so as to have a concentration of 5% by weight, and the solution was transferred onto a Teflon (registered trademark) petri dish and dried at normal pressure and room temperature for one day and night. This was dried under reduced pressure to obtain a film composed of LA/CL copolymer.

Immobilization with Peptide

The obtained polymer film was cut into 1 cm square, placed in a 1.5 mL size low adsorption tube (Eppendorf), and 1 mL of the peptide solution for immobilization prepared in the same manner as in Example 1 was added thereto. After allowing to stand at room temperature overnight, the film was transferred to a newly prepared 1.5 mL size low adsorption tube, then an operation of adding 1 mL of ion-exchanged water and removing it was repeated three times for washing, and then air-dried, to obtain a cell adhesive film in which a peptide group in which lysine/phenylalanine were randomly arranged was immobilized on the surface. The obtained film was placed in a 12-well plate, and the cell adhesion ratio was evaluated according to Measurement Example 4.

Example 9

A cell adhesive film was obtained in the same manner as in Example 8 except that, as a peptide group, a peptide solution for immobilization was prepared using a peptide (weight average molecular weight 1,417) consisting of 10 amino acid residues, a sequence in which lysine residues and phenylalanine residues are alternately repeated, which was synthesized by entrusting to Sigma-Aldrich Co., Ltd.

Comparative Example 2

A cell adhesive film was obtained in the same manner as in Example 8 except that a peptide solution for immobilization was prepared using commercially available polylysine (weight average molecular weight 22,500) (Sigma-Aldrich) as a peptide group.

Example 10

A cell culture plate was obtained in the same manner as in Example 4 except for changing the amount to 291 mg of N-Cbz-Lys-NPC, and using 71 mg of Gly-NPC (WATANABE CHEMICAL) and 91 mg of Leu-NPC (WATANABE CHEMICAL) instead of Phe-NPC. The weight average molecular weight and the content of amino acid residues were measured using a sample prepared by dissolving 169.1 mg of the obtained group of peptides with protecting groups in 4.8 mL of trifluoroacetic acid.

Example 11

A cell culture plate was obtained in the same manner as in Example 10 except that 112 mg of Asp-NPC (WATANABE CHEMICAL) was used instead of Leu-NPC. The weight average molecular weight and the content of amino acid residues were measured using a sample prepared by dissolving 158.9 mg of the obtained group of peptides with protecting groups in 4.5 mL of trifluoroacetic acid.

Example 12

A cell culture plate was obtained in the same manner as in Example 10 except for changing the amount to 241 mg of N-Cbz-Lys-NPC, 59 mg of Gly-NPC, 76 mg of Leu-NPC, and 93 mg of Asp-NPC. The weight average molecular weight and the content of amino acid residues were measured using a sample prepared by dissolving 139.7 mg of the obtained peptide group with a protecting group in 4.0 mL of trifluoroacetic acid.

Example 13

A cell culture plate was obtained in the same manner as in Example 7 except for changing phenylalanine to leucine.

Example 14

A cell culture plate was obtained in the same manner as in Example 7 except for changing phenylalanine to valine.

Example 15

A cell culture plate was obtained in the same manner as in Example 7 except for changing lysine to arginine.

Example 16

A cell culture plate was obtained in the same manner as in Example 13 except for changing lysine to arginine.

Example 17

A cell culture plate was obtained in the same manner as in Example 14 except for changing lysine to arginine.

Comparative Example 3

A cell culture plate was obtained in the same manner as in Example 12 except for changing the amount to 162 mg of N-Cbz-Lys-NPC, 79 mg of Gly-NPC, 102 mg of Leu-NPC, and 125 mg of Asp-NPC. The weight average molecular weight and the content of amino acid residues were measured using a sample prepared by dissolving 76.2 mg of the obtained peptide group with a protecting group in 2.2 mL of trifluoroacetic acid.

Table 1 shows information of the peptide and substratum and the peptide immobilization density and cell adhesion ratio of the obtained substrates in Examples and Comparative Examples.

Comparative Example 4

A cell culture plate was obtained in the same manner as in Example 7 except that, as a peptide group, a peptide solution for immobilization was prepared using a peptide (weight average molecular weight 1,146) consisting of 9 amino acid residues, a sequence in which an arginine residue, a glycine residue and an aspartic acid residue are repeated three times in this order, which was synthesized by entrusting to Sigma-Aldrich Co., Ltd.

TABLE 1

| | Substratum | | Composition of amino acid residues | Sequence | Peptide group Basic amino acid content (%) | Hydrophobic amino acid content (%) | Weight average molecular weight | Cell adhesive substrate Peptide immobilization density Y ($\mu g/cm^2$) | Cell adhesion ratio (%) |
|---|---|---|---|---|---|---|---|---|---|
| | Material | Shape | | | | | | | |
| Example 1 | Polystyrene | Cell culture plate | Lysine/phenylalanine | Random | 55 | 45 | 14845 | 0.114 | 53% |
| Example 2 | Polystyrene | Cell culture plate | Lysine/phenylalanine | Random | 53 | 47 | 30224 | 0.106 | 50% |
| Example 3 | Polystyrene | Cell culture plate | Lysine/phenylalanine | Random | 51 | 49 | 8325 | 0.107 | 58% |
| Example 4 | Polystyrene | Cell culture plate | Lysine/phenylalanine | Random | 54 | 46 | 5834 | 0.087 | 53% |
| Example 5 | Polystyrene | Cell culture plate | Lysine/phenylalanine | Random | 46 | 54 | 5000 | 0.117 | — |
| Example 6 | Polystyrene | Cell culture plate | Lysine/phenylalanine | Random | 75 | 25 | 5000 | 0.053 | — |
| Example 7 | Polystyrene | Cell culture plate | Lysine/phenylalanine | Alternating | 50 | 50 | 1417 | 0.067 | 41% |
| Comparative Example 1 | Polystyrene | Cell culture plate | Lysine | — | 100 | 0 | 22500 | 0.036 | 52% |
| Example 8 | PCL/PLA | Film | Lysine/phenylalanine | Random | 46 | 54 | 5000 | 0.247 | 56% |
| Example 9 | PCL/PLA | Film | Lysine/phenylalanine | Alternating | 50 | 50 | 1417 | 0.090 | — |
| Comparative Example 2 | PCL/PLA | Film | Lysine | — | 100 | 0 | 22500 | 0.032 | — |
| Example 10 | Polystyrene | Cell culture plate | Lysine/glycine/leucine | Random | 54 | 46 | 5905 | — | 46% |
| Example 11 | Polystyrene | Cell culture plate | Lysine/glycine/aspartic acid | Random | 54 | 25 | 6383 | — | 43% |
| Example 12 | Polystyrene | Cell culture plate | Lysine/glycine/leucine/aspartic acid | Random | 44 | 36 | 6258 | — | 38% |

TABLE 1-continued

| | Substratum | | Composition of amino | | Peptide group | | | Cell adhesive substrate | |
|---|---|---|---|---|---|---|---|---|---|
| | | | | | Basic amino acid content (%) | Hydrophobic amino acid content (%) | Weight average molecular weight | Peptide immobilization density Y (μg/cm²) | Cell adhesion ratio (%) |
| | Material | Shape | acid residues | Sequence | | | | | |
| Example 13 | Polystyrene | Cell culture plate | Lysine/leucine | Alternating | 50 | 50 | 1249 | — | 66% |
| Example 14 | Polystyrene | Cell culture plate | Lysine/valine | Alternating | 50 | 50 | 1179 | — | 34% |
| Example 15 | Polystyrene | Cell culture plate | Arginine/phenylalanine | Alternating | 50 | 50 | 1559 | — | 57% |
| Example 16 | Polystyrene | Cell culture plate | Arginine/leucine | Alternating | 50 | 50 | 1389 | — | 73% |
| Example 17 | Polystyrene | Cell culture plate | Arginine/valine | Alternating | 50 | 50 | 1319 | — | 44% |
| Comparative Example 3 | Polystyrene | Cell culture plate | Lysine/glycine/leucine/ aspartic acid | Random | 29 | 48 | 7408 | — | 7% |
| Comparative Example 4 | Polystyrene | Cell culture plate | Arginine/glycine/ aspartic acid | Permutation | 33 | 33 | 1146 | — | 12% |

The invention claimed is:

1. A cell adhesive substrate comprising a substratum, on a surface of which a peptide group is immobilized, wherein
   the peptide group comprises a peptide containing 40% or more and 75% or less of one or two or more of basic amino acid residues selected from the group consisting of lysine, arginine and histidine and 25% or more of one or two or more of hydrophobic amino acid residues selected from the group consisting of leucine, isoleucine, glycine, alanine, valine, phenylalanine, proline, tryptophan and methionine, and
   the peptide group is a set of peptides consisting of the basic amino acid residues and the hydrophobic amino acid residues.

2. The cell adhesive substrate according to claim 1, wherein the peptide group consists of peptides without an ordered amino acid sequence.

3. The cell adhesive substrate according to claim 1, wherein the peptide group contains 40% or more and 75% or less of lysine or arginine residues, and contains 25% or more of any of phenylalanine, leucine and valine residues.

4. The cell adhesive substrate according to claim 1, wherein an immobilization density of the peptide group on the surface of the substratum is 0.040 μg/cm² or more.

5. The cell adhesive substrate according to claim 1, wherein the peptide is adsorbed on the surface of the substratum without a chemical bond.

6. The cell adhesive substrate according to claim 5, wherein the peptide is adsorbed on the surface of the substratum only by hydrophobic interaction.

7. The cell adhesive substrate according to claim 1, wherein the peptide group has a weight average molecular weight of 1,000 or more and 30,000 or less.

8. The cell adhesive substrate according to claim 1, wherein the substratum comprises a material selected from polylactic acid, polyglycolic acid, polycaprolactone, polylactide glycoside, polyether ether ketone, polyvinyl chloride, polystyrene, polyethylene terephthalate and polybutylene terephthalate and copolymers thereof.

9. The cell adhesive substrate according to claim 1, wherein the substratum comprises a copolymer of two or more of monomers selected from the group consisting of lactic acid, caprolactone and glycolic acid.

* * * * *